United States Patent [19]

Mori

[11] Patent Number: 4,865,035

[45] Date of Patent: Sep. 12, 1989

[54] LIGHT RAY RADIATION DEVICE FOR USE IN THE MEDICAL TREATMENT OF THE EAR

[76] Inventor: Kei Mori, 3-16-3-501, Kaminoge, Setagaya-ku, Tokyo, Japan

[21] Appl. No.: 126,149

[22] Filed: Nov. 30, 1987

[30] Foreign Application Priority Data

Apr. 7, 1987 [JP] Japan .................................. 62-85462

[51] Int. Cl.$^4$ .............................................. A61N 3/00
[52] U.S. Cl. ................................... 128/398; 128/380; 362/105
[58] Field of Search ............................... 128/395–398, 128/23, 9, 374, 380, 24.1; 362/32, 103–106

[56] References Cited

U.S. PATENT DOCUMENTS

| | | | |
|---|---|---|---|
| 1,741,313 | 12/1929 | Kelley ................................ | 128/395 |
| 4,211,229 | 7/1980 | Wurster ............................. | 128/395 |
| 4,570,635 | 2/1986 | Henig ................................. | 128/380 |
| 4,658,823 | 4/1987 | Beddoe .............................. | 128/396 |

FOREIGN PATENT DOCUMENTS

| | | | |
|---|---|---|---|
| 3431629 | 3/1986 | Fed. Rep. of Germany ...... | 128/395 |
| 338679 | 10/1903 | France ................................ | 128/396 |
| 1139096 | 6/1957 | France ................................ | 128/395 |

*Primary Examiner*—Edward M. Coven
*Assistant Examiner*—Mark S. Graham

[57] ABSTRACT

A light ray radiation device for use in the medical treatment of the ear comprises an optical conductor cable, an elongated light radiator, a pair of light radiator holders, and a fixing means. The optical conductor cable transmits therethrough the light rays corresponding to the visible light ray components of the sun or an artificial light source having the wave length distribution of the light rays near the sun's rays. The elongated light radiator is removably connected with the light-emitting end of the optical conductor cable for uniformly discharging the light rays transmitted through the optical conductor cable. The pair of light radiator holders holds the light radiator so as to be able to move the same in the direction of the axis and covers the concha. And the fixing means such as a band or the like fixes the pair of light radiator holders by causing them to press against each other.

9 Claims, 5 Drawing Sheets

FIG.4
FIG.5
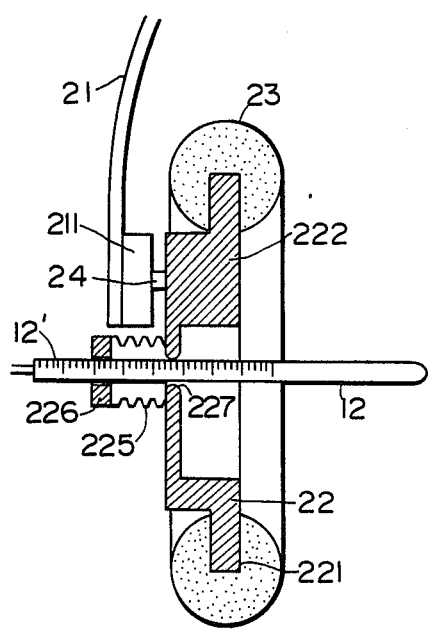
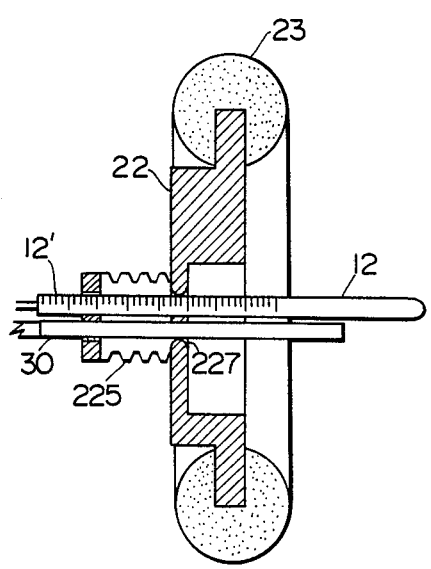

LIGHT RAY RADIATION DEVICE FOR USE IN THE MEDICAL TREATMENT OF THE EAR

BACKGROUND OF THE INVENTION

The present invention relates to a light ray radiation device for use in the medical treatment of the ear, and in particular, a light ray radiation device for use in medical treatment capable of radiating the light ray components corresponding to the visible light rays contained in the sun's rays onto any diseased part of the ear from the external ear passage to the middle ear.

The present applicant has previously proposed various ways to focus the sun's rays or artificial light rays by use of lenses or the like and to guide the same into an optical conductor cable and thereby to transmit and emit the same onto an optional desired place through an optical conductor. The sun's rays or the artificial light rays transmitted and emitted in such a way are employed for illumination or for other like purposes, as for example, for cultivating plants, chlorella or the like. In the process of doing the above the visible light rays containing therein neither ultraviolet rays nor infrared rays promote the health of a person by creating a living body reaction or the same prevents the skin of a human from growing old. Furthermore, the visible light ray components have noticeable effects for recovering from arthritis, neuralgia, bedsores, rheumatism, burns, skin diseases, injuries, bone fractures, or the like and for alleviating pain from those diseases. Such beneficial effects have been witnessed by the present applicant.

On the basis of the above-mentioned discovery, the present applicant has previously proposed in various ways light ray radiation devices for use in medical treatment which are capable of administering various kinds of medical treatment or beauty treatment or for promoting the health of a human body by radiating the light rays corresponding to the visible light ray components of the sun and containing therein no harmful components such as ultraviolet rays, infrared rays or the like.

A light ray radiation device for use in medical treatment previously proposed by the present applicant comprises an optical conductor cable, a semi-transparent cylindrical member, and a cover member. The sun's rays or artificial light rays having a wave length distribution similar to that of the sun's rays are guided into the optical conductor cable at the end portion thereof, and the guided light rays are transmitted therethrough. The light rays corresponding to the visible light ray components of the sun's rays (the white colored ones), are transmitted into the optical conductor cable in a manner previously proposed by the present applicants various ways. The semi-transparent cylindrical member is furnished at the light-emitting end side of the aforementioned optical conductor cable, and the cover member is furnished to close one end side of the cylindrical member. The light-emitting end side of the optical conductor cable is attached to the cover member at the approximate central portion thereof. The solar ray energy transmitted through the optical conductor cable is discharged into the cylindrical member. At the time of administering medical treatment, the other end side of the cylindrical member is put on the part of a patient to be treated, or the same is placed so as to be opposite to the same part and at a desired interval therefrom. The light rays consisting of the visible light ray components transmitted through the optical conductor cable in such a manner as mentioned before, are radiated onto the diseased part, i.e., the desired portion, or the other parts of the body needing treatment. The light rays to be radiated onto the diseased part of a patient in such a way are the light rays corresponding to the visible light ray components of the sun's rays. Consequently, it becomes possible to administer medical treatment without exposing a patient to the harmful effects of ultraviolet or infrared rays.

SUMMARY OF THE INVENTION

The object of the present invention is to provide a visible light ray radiation device for use in the medical treatment of the ear capable of radiating light rays onto a diseased part of a human body, as for example, the external ear or the external ear.

Another object of the present invention to provide a device for use in the medical treatment of the external ear and the internal ear capable administering with certainty and safety by radiating the light rays consisting of the visible light ray components of the sun's rays onto the diseased part of the patient's ear.

BRIEF DESCRIPTION OF THE DRAWINGS

FIGS. 4 and 5 are views for explaining respectively other embodiments of the present invention;

DESCRIPTION OF THE PREFERRED EMBODIMENTS

Figure 1:
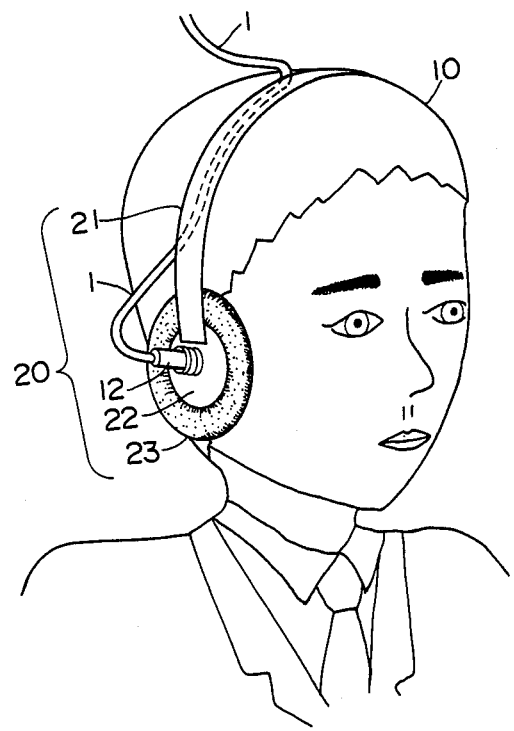
FIG. 1 is a perspective view showing a state in which a patient is equipped with a light ray radiation device for use in medical treatment.

FIG. 1 is a perspective view showing a state in which a patient 10 employs a light ray radiation device for use in medical treatment 20. The light ray radiation device 20 uniformly radiates the light rays corresponding to the visible light ray components of the sun's rays transmitted through the optical conductor cable 1 from a light radiator 12 which is removably attached to the light-emitting end of the optical conductor cable 1 and inserted into the external ear passage of a patient 10. The light rays are radiated onto the external ear or the internal ear of a patient and the blood circulation becomes improved at the radiated portion, so that a living body (tissue cell) reaction is promoted and the effect of medical treatment is improved.

The light radiator 12 is located at the approximate central portion of a light radiator holder 22 and removably attached thereto with the flexibility of being capable of fitting to and inserting into the external ear passage of a patient. The light radiator holder 22 is constructed with, for instance, a trapezoidal ring, and an ear cover 23 is disposed on the outer circumference thereof. Consequently, the light radiator can be supported stably in the external ear passage by convering the external portion of the concha (pinna) by use of an ear cover 23. A resilient band 21 made of spongy material coated with, for instance, resin or the like is rotatably attached to the light radiator holder 22. The band 21 connects the left and right light radiators with each other. The band 21 suspended from the head is adjusted so as to softly press the left and right conchas. Moreover, the optical conductor cable 1 makes contact with the light radiator 12 along, a band 21 from a sun ray guiding device not shown in FIG. 1.

Figure 2:
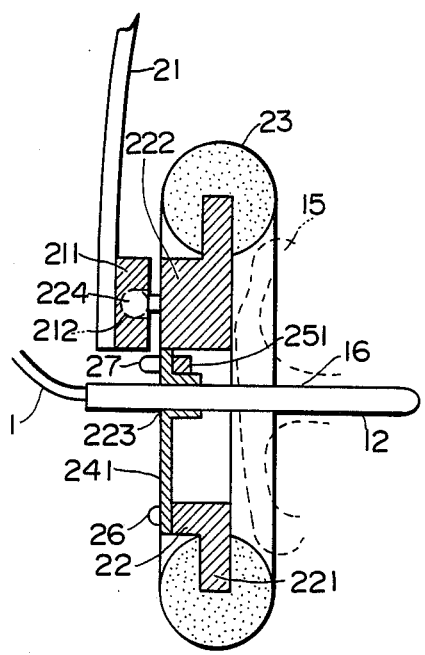
FIGS. 2 and 3 are views for showing an embodiment of a light ray radiation device according to the patent invention.
Figure 3:
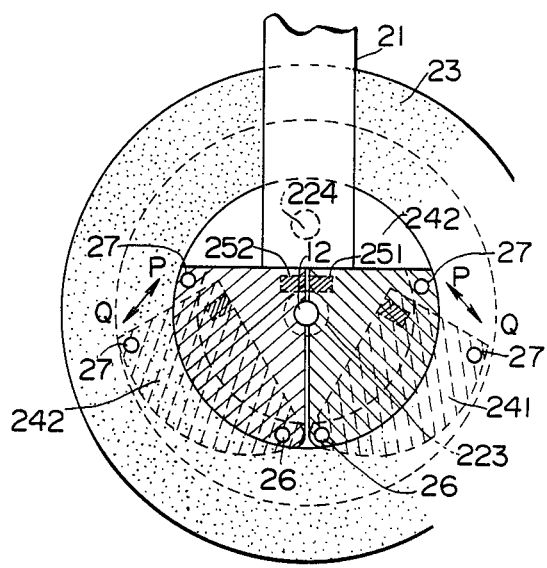

FIG. 2 is a side cross-sectional view for explaining the details of the light ray radiation device for use in medical treatment 20 shown in FIG. 1, and FIG. 3 is a front view of the light ray radiation device 20 as seen from the outside. In FIGS. 2 and 3, the same reference numeral as that of FIG. 1 is given to the construction element that has something in common with that of FIG. 1. The light radiator holder 22 consists of a trapezoidal ring made of, for example, resin and has an opening portion in the internal side thereof. The concha 15 of the patient is accommodated in the internal side thereof. A coated porous sponge-like ring 23 for receiving an ear cover is placed on the external circumferential portion brought into contact with the external portion of the concha 15, so that any pain is lessened at the time of attaching the ring 221 to the concha 15.

A semi-lunar solid band supporting portion 222 is mounted on the upper opening portion of the light radiator holder 22, and a band supporting pin 224 is buriedly attached to the band supporting portion so as to be rotatably joined with the band 21. The other end of the band supporting pin 224 is spherical. The spherical portion of the band supporting pin 224 is pressedly inserted into and slidably joined with a pin receiving seat 212 bored in a supporting pin receiving portion 211 fixedly attached to the end portion of the band. A pair of holding-plates 241 and 242 for rotatably holding the light radiator holder 12, when it is inserted into the external ear passage, are installed under the outer circumference of the light radiator holder 22 as to enable it to be opened and closed around an axis pin 26 (therefore two pins are shown in FIG. 3.). The holding plates 241 and 242 are of the same shape and equal dimension, and the same are made of transparent resin a little larger than a quadrant. A semi-cylindrical light radiator holding portion 223 is installed on the central portion of the light radiator holder 22 at the respective opening/closing joint portion of the holding plates 241 and 242. The light radiator 12 is clippingly held in the semi-cylindrical holding portion of the holding plates by rotating the holding plates 241 and 242 in a closing direction P and the light radiator 12 is removed by rotating the holding plates 241 and 242 to an opening direction Q around the axis pin 26. Since the cylindrical surface of the light radiator holding portion 223 is formed in a tapered shape, the light radiator can rotate around the portion it comes in contact with directly.

Moreover, the closure of the holding plates 241 and 242 is performed by the action of a magnetic force generated by magnets 251 and 252 buriedly mounted on a place near the joint portion of the holding plates 241 and 242, and further the light radiator is clippingly held by the action of the magnetic force generated thereby. At the time of rotating the holding plates 241 and 242 in a direction or in two (directions), Q to open them, handles 27 buriedly mounted respectively on each outer circumferential portion of the holding plates are rotated by finger pressure. Since the light radiator 12 is clippingly held by the action of the magnetic force, it may be possible to insert the light radiator 12 into an optimum position and draw out the same therefrom, by observing the position of the external ear passage through the transparent holding plates 241 and 242.

FIG. 4 is a side cross-sectional view for explaining another embodiment of the present invention. The method of holding the light radiator 12 shown in FIG. 4 differs from that of the embodiment shown in FIG. 2. A round opening portion 227, having a cross-section a little smaller than the outer diameter of the light radiator 12, is formed at the central portion of the light radiator holder 22 and the light radiator is inserted through the round open portion 227 and fixedly held at a certain position thereafter. The cross-section of the inner circumferential surface of the round opening portion 227 is semi-circular, and the light radiator 12 can rotate around the holding position thereof. And further, a bellows 225, having a support ring 226 fixedly attached to one end thereof, is joined with the outside of the round opening portion 227, and thereby it may be possible to support the light radiator 12 on the respective inner circumferences of the support ring 226 and the round opening portion 227 connected with each other by the use of bellows 225. In such a way, the light radiator can be supported with a flexibility and stably. Moreover, since the light radiator holder 22 is made of a transparent resin, the position of the light radiator 12 in the external ear passage can be seen with the naked eye.

FIG. 5 is a side cross-sectional view for explaining still another embodiment of the present invention. In the embodiment of FIG. 5, when the light radiator 12 cannot be seen with the naked eye, a bundle-shaped optical fiber 30 is additionally installed in parallel with the light radiator 12 in order to make it possible to see it with the naked eye, and thereby the insertion position of the light radiator 12 can be observed directly by means of an optical system not shown in FIG. 5 which is connected with the external joint portion of the bundle-shaped optical fiber 30. Moreover, it may be possible to put a scale 12' on the outer circumference of the light radiator 12 along the axis direction thereof.

Figure 6:
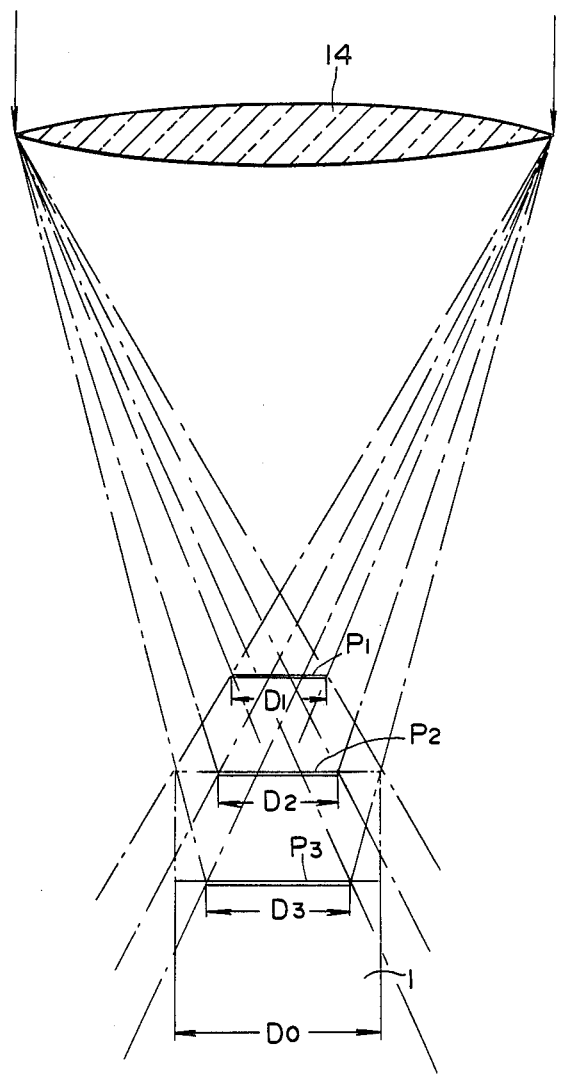
FIG. 6 is an optional explanatory view for explaining an embodiment of the visible light ray collecting method applied to the use of the present invention.

FIG. 6 is an explanatory view for explaining an embodiment of the device for guiding the afore-mentioned light rays corresponding to the visible light ray components of the sun's rays into the optical conductor cable 1. In FIG. 6, 14 is a lens system consisting of a Fresnel lens or the like, and 1 is an optical conductor cable as mentioned before for guiding thereinto the sun's rays focused by the lens system 14 and transmitting the guided rays therethrough. In the case of focusing the sun's rays by use of a lens system, the solar image has a central portion consisting of almost white-colored light rays and a circumferential portion containing therein a large amount of light ray components consisting of the needed wave lengths for focusing the lens system.

Namely, in the case of focusing the sun's rays by means of the lens system, the focal position of the lens system and the size of the solar image will vary in accordance with the wave length of the light rays. For instance, the light rays of the color blue having a short wave length make a solar image of diameter $D_1$ at position $P_1$. And further, the light rays of the color green make a solar image of diameter $D_2$ at position $P_2$ and the light rays of the color red make a solar image of diameter $D_3$ at position $P_3$.

Consequently, as shown in FIG. 6, when the lightreceiving end-surface of the optical conductor cable 1 is put at the position P₁, it is possible to collect sun's rays containing circumferential portion thereof. When the same is put at position P₂, it is possible to collect the sun's rays containing plenty of light rays of the green color component at the circumferential portion thereof. When the same is put at position P₃, it is possible to collect the sun's rays containing plenty of light rays of the red color component at the circumferential portion thereof. In each case, the diameter of the optical conductor cable is determined by the light ray components to be collected. For instance, the diameters thereof are D₁, D₂ and D₃, respectively, depending on the colors of the light rays to be stressed; the blue, green and red colors. In such a way, the consumed amount of the optical conductor cable can be reduced, and thereby the sun's rays containing plenty of light ray components of the desired color can be collected most effectively. And further, as shown in FIG. 6, if the diameter of the light-receiving end surface of the optical conductor cable 1 is enlarged to D₀, it may be possible to collect visible light rays containing components of all of the wave lengths.

Figure 7:
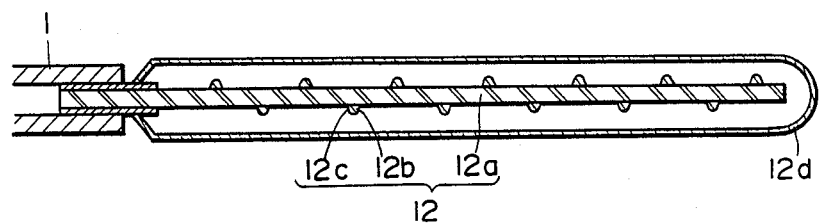
FIG. 7 is an explanatory view for explaining an embodiment of the light radiator as used with the present invention.

FIG. 7 is an explanatory view for explaining an embodiment of the afore-mentioned light radiator 12. However, the light radiator employed in the present invention is not limited to the one as shown in FIG. 7. In FIG. 7, the light radiator 12 comprises an optical conductor 12a, adhesive such as epoxy resin 12b bonded to the outer circumferential portion of the optical conductor 12a almost at uniform intervals of distance and having the refraction index equal to or larger than that of the optical conductor 12a, and a transparent cover member 12d for covering the optical conductor 12a, to which the adhesive 12b is bonded. The light radiator 12 is connected with the light-emitting end of the optical conductor cable 1 and employed for radiating light rays at the time of administering medical treatment.

Consequently, the light rays transmitted through the optical conductor cable 1 are guided into the optical conductor 12a of the light radiator 12 and propagate through the optical conductor 12a toward teh end portion thereof. During the time of propagation, the light rays are refracted in the adhesive layer portion 12c and discharged outside of the optical conductor 12a. The light rays radiated in such a way are employed for administering medical treatment of the diseased part in the ear hole as mentioned before. Needless to say various sizes and shapes of light radiators 12 are provided in accordance with the size of the external ear passage of each patient. An appropriate light radiator is selected among them and employed.

Figure 8:
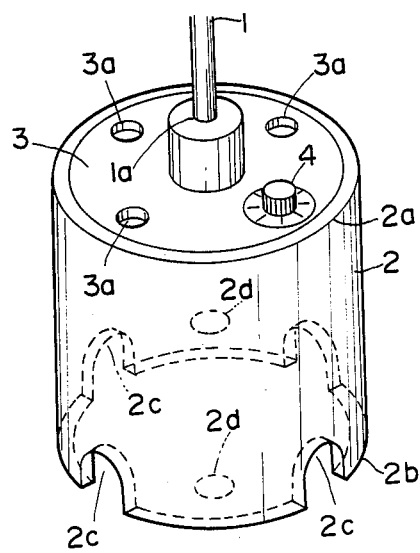
FIG. 8 is an explanatory view for explaining an embodiment of the light ray radiation device for use in medical treatment previously proposed by the present applicant.

FIG. 8 is a construction view for explaining an embodiment of a light ray radiation device for use in medical treatment previously proposed by the present applicant. In FIG. 8, 1 is an optical conductor cable. The sun's rays or artificial light rays having a wave length distribution similar to that of the sun's rays are guided into the optical conductor cable 1 at the end portion thereof (not shown in FIG. 8), and the guided light rays are transmitted therethrough. The light rays corresponding to the visible light ray components of the sun's rays (the white colored ones), are transmitted into the optical conductor cable 1 in a manner previously proposed by the present applicants in various ways. In FIG. 8, 2 is a semitransparent cylindrical member furnished at the light-emitting end i.e. side 1a of the afore-mentioned optical conductor cable 1, and 3 is a cover member for closing one end side 2a of the cylindrical member 2. The light-emitting end side 1a of the optical conductor cable 1 is attached to the cover member 3 at the approximate central portion thereof. The solar ray energy transmitted through the optical conductor cable 1 is discharged into the cylindrical member 2. At the time of administering medical treatment, the other end side 2b of the cylindrical member is put on the part of a patient to be treated, or the same is placed so as to opposite to the same part and at a desired interval therefrom. The light rays consisting of the visible light ray components transmitted through the optical conductor cable 1 in such a manner as mentioned before, are radiated onto the diseased part, i.e. the desired portion, or the other parts of the body needing treatment. The light rays to be radiated onto the diseased part of a patient in such a way are the light rays corresponding to the visible light ray components of the sun's rays. Consequently, it becomes possible to administer medical treatment without exposing a patient to the harmful effects of ultraviolet or infrared rays.

As is apparent from the foregoing description, according to the present invention, the medical treatment of the external ear and the internal ear can be administered with certainty and safety by radiating the light rays consisting of the visible light ray components of the sun's rays onto the diseased part of the patient's ear.

I claim:

1. A light ray radiation device for use in medical treatment of a person's ear comprising an optical conductor cable for transmitting therethrough the light rays corresponding to the vixible light ray components of the sun or an artificial light source, said cable having a longitudinal end portion, an elongated light radiator removably connected to said end portion, said light radiator receiving light rays from said cable and uniformly emitting said light rays, a holder for holding said light radiator, said holder comprising a ring member having an outer circumference, a ring-shaped ear cover mounted on said outer circumference of said ring member, said ear cover being adapted to cover the concha of a person's ear being treated, said ring member having an opening, said light radiator passing through said opening and being slidably supported in said opening, and a support band connected to said ring member and adapted to pass over the head of said person being treated, whereby said support band and said ear cover support said ring member juxtaposed to said person's ear as said light radiator is slidably supported by said ring member as said light radiator effects treatment of said person's ear.

2. A light ray radiation device according to claim 1, wherein said ear cover is made of a sponge material.

3. A light ray radiation device according to claim 1, wherein said support band is connected to said ring member by a connecting means comprising a spherical ball element extending from said ring member and a ball-receiving seat in said support band for receiving said spherical ball element, said spherical ball element being movable in said ball-receiving seat.

4. A light ray radiation defice for use in medical treatment of a person's ear comprising an optical conductor cable for transmitting therethrough the light rays corresponding to the visible light ray components of the sun or an artificial light source, said cable having a longitudinal end portion, an elongated light radiator removably connected to said end portion, said light radiator receiving light rays from said cable and uniformly emitting said light rays, a holder for holding said light radiator such that said light radiator is movable longitudinally relative to said holder, said holder being adapted to cover the concha of a person's ear being treated, said holder comprising a ring member having an outer circumference, a ring-shaped ear cover disposed on said outer circumference of said ring member, said ring member having an opening, said light radiator passing through said opening, a pair of transparent holding plates, pivot pins pivotably mounting said holding plates on said ring member for pivotal movement about said pivot pins between a closed position and an open position, said holding plates each having a semi-cylindrical portion such that when said holding plates are in said closed position, said holding plates close off said opening and said semi-cylindrical portions mate to form a cylindrical portion for holding said light radiator, and magnet means on each of said holding plates for holding said plates in said closed position.

5. A light ray rediation device according to claim 4, wherein said holding plates have approximately the same size and configuration.

6. A light ray radiation device according to claim 4, wherein said light radiator has a generally cylindrical configuration, said holding plates each having a generally linear mating edge surface which mate with each other when in said closed position, said linear mating edge surfaces being disposed along a diametric line passing through the center of said light radiator when in said closed position.

7. A light ray radiation device according to claim 4 further comprising a head band, and movable connecting means movably connecting said head band to said ring member.

8. A light ray radiation device for use in medical treatment of a person's ear comprising an optical conductor cable for transmitting therethrough the light rays corresponding to the visible light ray components of the sun or an artificial light source, said cable having a longitudinal end portion, an elongated light radiator removably collected to said end portion, said light radiator receiving light rays from said cable and uniformly emitting said light rays, a holder for holding said light radiator such that said light radiator is movable longitudinally relative to said holder, said holder being adapted to cover the concha of a person's ear being treated, said holder comprising a ring member having an outer circumference, a ring-shaped ear cover disposed on said outer circumference of said ring member, said ring member having a lower portion made of a transparent material, a round opening in said lower portion, said light radiator having a generally cylindrical configuration, said light radiator extending through said round opening, a bellows having a longitudinal axis, said bellows having one longitudinal end mounted on said lower portion of said ring member, said bellows being generally axially aligned with said round opening, said bellows having a support ring on its other longitudinal end, said support ring having a support ring opening, said light radiator being longitudinally slidably and rotatably mounted in said support ring opening in said support ring of said bellows and in said round opening of said transparent lower portions of said ring member.

9. A light ray radiation device according to claim 8, wherein said support ring opening is axially aligned with said round opening.

* * * * *